US011291252B2

United States Patent
Sur et al.

(10) Patent No.: US 11,291,252 B2
(45) Date of Patent: Apr. 5, 2022

(54) PROXIMITY SENSING FOR AN AEROSOL DELIVERY DEVICE

(71) Applicant: R.J. REYNOLDS TOBACCO COMPANY, Winston-Salem, NC (US)

(72) Inventors: Rajesh Sur, Winston-Salem, NC (US); Stephen B. Sears, Siler City, NC (US); Michael F. Davis, Clemmons, NC (US)

(73) Assignee: RAI Strategic Holdings, Inc., Winston-Salem, NC (US)

( * ) Notice: Subject to any disclaimer, the term of this patent is extended or adjusted under 35 U.S.C. 154(b) by 491 days.

(21) Appl. No.: 14/975,121

(22) Filed: Dec. 18, 2015

(65) Prior Publication Data
US 2017/0181223 A1 Jun. 22, 2017

(51) Int. Cl.
*H05B 3/00* (2006.01)
*A24F 47/00* (2020.01)
(Continued)

(52) U.S. Cl.
CPC .............. *A24F 40/65* (2020.01); *A24F 40/50* (2020.01); *A61M 11/042* (2014.02);
(Continued)

(58) Field of Classification Search
USPC ....................................................... 392/404
See application file for complete search history.

(56) References Cited

U.S. PATENT DOCUMENTS

| 1,771,366 A | 7/1930 | Wyss et al. |
| 2,057,353 A | 10/1936 | Whittemore, Jr. |

(Continued)

FOREIGN PATENT DOCUMENTS

| AU | 276250 | 7/1965 |
| CA | 2 641 869 | 5/2010 |

(Continued)

OTHER PUBLICATIONS

International Search Report dated May 9, 2017 for Application No. PCT/IB2016/057734.
(Continued)

*Primary Examiner* — Ibrahime A Abraham
*Assistant Examiner* — Gyounghyun Bae
(74) *Attorney, Agent, or Firm* — Womble Bond Dickinson (US) LLP (57) ABSTRACT

A control body is coupled or coupleable with a cartridge that is equipped with a heating element and contains an aerosol precursor composition, the control body and cartridge forming an aerosol delivery device. The control body includes a control to control the heating element to activate and vaporize components of the aerosol precursor composition. The proximity sensor detects a presence of an object nearby the control body without requiring any physical contact with the object. And the proximity sensor or control component controls operation of at least one functional element of the aerosol delivery device in response to the presence of the object so detected. In another aspect, a cartridge may include a proximity sensor to detect a level of the aerosol precursor composition, and operation of functional element(s) may be controlled in response to the level of the aerosol precursor composition so detected.

14 Claims, 3 Drawing Sheets

(51) Int. Cl.

| | | |
|---|---|---|
| *H04W 4/02* | (2018.01) | |
| *A24F 40/65* | (2020.01) | |
| *H04L 67/01* | (2022.01) | |
| *A61M 15/06* | (2006.01) | |
| *A61M 11/04* | (2006.01) | |
| *H04B 5/00* | (2006.01) | |
| *H04L 67/12* | (2022.01) | |
| *A24F 40/50* | (2020.01) | |
| *G01F 23/263* | (2022.01) | |
| *A61M 15/00* | (2006.01) | |
| *A61M 16/00* | (2006.01) | |
| *H02J 50/10* | (2016.01) | |
| *A24F 40/10* | (2020.01) | |

(52) U.S. Cl.
CPC .......... *A61M 15/06* (2013.01); *H04B 5/0081* (2013.01); *H04L 67/12* (2013.01); *H04L 67/42* (2013.01); *H04W 4/025* (2013.01); *H05B 3/0014* (2013.01); *A24F 40/10* (2020.01); *A61M 15/008* (2014.02); *A61M 15/0081* (2014.02); *A61M 15/0083* (2014.02); *A61M 2016/0024* (2013.01); *A61M 2016/0039* (2013.01); *A61M 2205/127* (2013.01); *A61M 2205/13* (2013.01); *A61M 2205/14* (2013.01); *A61M 2205/27* (2013.01); *A61M 2205/3368* (2013.01); *A61M 2205/3389* (2013.01); *A61M 2205/3592* (2013.01); *A61M 2205/3653* (2013.01); *A61M 2205/50* (2013.01); *A61M 2205/6018* (2013.01); *A61M 2205/6054* (2013.01); *A61M 2205/8206* (2013.01); *A61M 2205/8212* (2013.01); *G01F 23/263* (2013.01); *H02J 50/10* (2016.02); *H04B 5/0037* (2013.01); *H04B 5/0062* (2013.01)

(56) References Cited

U.S. PATENT DOCUMENTS

| | | | |
|---|---|---|---|
| 2,104,266 | A | 1/1938 | McCormick |
| 3,200,819 | A | 8/1965 | Gilbert |
| 4,284,089 | A | 8/1981 | Ray |
| 4,303,083 | A | 12/1981 | Burruss, Jr. |
| 4,735,217 | A | 4/1988 | Gerth et al. |
| 4,848,374 | A | 7/1989 | Chard et al. |
| 4,907,606 | A | 3/1990 | Lilja et al. |
| 4,922,901 | A | 5/1990 | Brooks et al. |
| 4,945,931 | A | 8/1990 | Gori |
| 4,947,874 | A | 8/1990 | Brooks et al. |
| 4,947,875 | A | 8/1990 | Brooks et al. |
| 4,986,286 | A | 1/1991 | Roberts et al. |
| 5,019,122 | A | 5/1991 | Clearman et al. |
| 5,042,510 | A | 8/1991 | Curtiss et al. |
| 5,060,671 | A | 10/1991 | Counts et al. |
| 5,093,894 | A | 3/1992 | Deevi et al. |
| 5,144,962 | A | 9/1992 | Counts et al. |
| 5,249,586 | A | 10/1993 | Morgan et al. |
| 5,261,424 | A | 11/1993 | Sprinkel, Jr. |
| 5,322,075 | A | 6/1994 | Deevi et al. |
| 5,353,813 | A | 10/1994 | Deevi et al. |
| 5,369,723 | A | 11/1994 | Counts et al. |
| 5,372,148 | A | 12/1994 | McCafferty et al. |
| 5,388,574 | A | 2/1995 | Ingebrethsen et al. |
| 5,408,574 | A | 4/1995 | Deevi et al. |
| 5,468,936 | A | 11/1995 | Deevi et al. |
| 5,498,850 | A | 3/1996 | Das |
| 5,515,842 | A | 5/1996 | Ramseyer et al. |
| 5,530,225 | A | 6/1996 | Hajaligol |
| 5,564,442 | A | 10/1996 | MacDonald et al. |
| 5,649,554 | A | 7/1997 | Sprinkel et al. |
| 5,666,977 | A | 9/1997 | Higgins et al. |
| 5,687,746 | A | 11/1997 | Rose et al. |
| 5,692,492 | A * | 12/1997 | Bruna ................. A61M 15/009 128/200.14 |
| 5,726,421 | A | 3/1998 | Fleischhauer et al. |
| 5,727,571 | A | 3/1998 | Meiring et al. |
| 5,743,251 | A | 4/1998 | Howell et al. |
| 5,799,663 | A | 9/1998 | Gross et al. |
| 5,809,997 | A * | 9/1998 | Wolf ................... A61M 15/009 128/200.23 |
| 5,819,756 | A | 10/1998 | Mielordt |
| 5,865,185 | A | 2/1999 | Collins et al. |
| 5,865,186 | A | 2/1999 | Volsey, II |
| 5,878,752 | A | 3/1999 | Adams et al. |
| 5,894,841 | A | 4/1999 | Voges |
| 5,934,289 | A | 8/1999 | Watkins et al. |
| 5,954,979 | A | 9/1999 | Counts et al. |
| 5,967,148 | A | 10/1999 | Harris et al. |
| 6,040,560 | A | 3/2000 | Fleischhauer et al. |
| 6,053,176 | A | 4/2000 | Adams et al. |
| 6,089,857 | A | 7/2000 | Matsuura et al. |
| 6,095,153 | A | 8/2000 | Kessler et al. |
| 6,125,853 | A | 10/2000 | Susa et al. |
| 6,155,268 | A | 12/2000 | Takeuchi |
| 6,164,287 | A | 12/2000 | White |
| 6,196,218 | B1 | 3/2001 | Voges |
| 6,196,219 | B1 | 3/2001 | Hess et al. |
| 6,598,607 | B2 | 7/2003 | Adiga et al. |
| 6,601,776 | B1 | 8/2003 | Oljaca et al. |
| 6,615,840 | B1 | 9/2003 | Fournier et al. |
| 6,688,313 | B2 | 2/2004 | Wrenn et al. |
| 6,772,756 | B2 | 8/2004 | Shayan |
| 6,803,545 | B2 | 10/2004 | Blake et al. |
| 6,854,461 | B2 | 2/2005 | Nichols |
| 6,854,470 | B1 | 2/2005 | Pu |
| 7,117,867 | B2 | 10/2006 | Cox et al. |
| 7,293,565 | B2 | 11/2007 | Griffin et al. |
| 7,513,253 | B2 | 4/2009 | Kobayashi et al. |
| 7,775,459 | B2 | 8/2010 | Martens, III et al. |
| 7,832,410 | B2 | 11/2010 | Hon |
| 7,845,359 | B2 | 12/2010 | Montaser |
| 7,896,006 | B2 | 3/2011 | Hamano et al. |
| 8,013,837 | B1 * | 9/2011 | Schroeder ............... G06F 3/011 345/157 |
| 8,127,772 | B2 | 3/2012 | Montaser |
| 8,314,591 | B2 | 11/2012 | Terry et al. |
| 8,365,742 | B2 | 2/2013 | Hon |
| 8,382,008 | B1 * | 2/2013 | Ricciardi ................. A61L 2/22 239/102.2 |
| 8,402,976 | B2 | 3/2013 | Fernando et al. |
| 8,499,766 | B1 | 8/2013 | Newton |
| 8,528,569 | B1 | 9/2013 | Newton |
| 8,550,069 | B2 * | 10/2013 | Alelov ................. A61M 11/005 128/202.21 |
| 9,861,299 | B1 * | 1/2018 | Jones ..................... A61B 5/097 |
| 2002/0043568 | A1 * | 4/2002 | Hess ....................... A61L 9/14 239/69 |
| 2002/0146242 | A1 | 10/2002 | Vieira |
| 2003/0140921 | A1 * | 7/2003 | Smith ..................... A61J 1/065 128/200.14 |
| 2003/0226837 | A1 | 12/2003 | Blake et al. |
| 2004/0118401 | A1 | 6/2004 | Smith et al. |
| 2004/0129280 | A1 | 7/2004 | Woodson et al. |
| 2004/0200488 | A1 | 10/2004 | Felter et al. |
| 2004/0226568 | A1 | 11/2004 | Takeuchi et al. |
| 2005/0016550 | A1 | 1/2005 | Katase |
| 2006/0016453 | A1 | 1/2006 | Kim |
| 2006/0030836 | A1 * | 2/2006 | Lee .................... A61M 5/14228 604/890.1 |
| 2006/0033508 | A1 * | 2/2006 | Lee ..................... G01R 27/2605 324/678 |
| 2006/0196518 | A1 | 9/2006 | Hon |
| 2007/0042305 | A1 * | 2/2007 | Muska ..................... F23Q 7/16 431/258 |
| 2007/0074734 | A1 | 4/2007 | Braunshteyn et al. |
| 2007/0102013 | A1 | 5/2007 | Adams et al. |
| 2007/0215167 | A1 | 9/2007 | Crooks et al. |
| 2008/0000477 | A1 * | 1/2008 | Huster ..................... A61B 5/01 128/204.23 |
| 2008/0085103 | A1 | 4/2008 | Beland et al. |

(56) References Cited

U.S. PATENT DOCUMENTS

| | | |
|---|---|---|
| 2008/0092912 A1 | 4/2008 | Robinson et al. |
| 2008/0230052 A1* | 9/2008 | Montaser .......... A61M 15/0085 128/200.16 |
| 2008/0231292 A1* | 9/2008 | Ossart ...................... G01B 7/08 324/688 |
| 2008/0257367 A1 | 10/2008 | Paterno et al. |
| 2008/0276947 A1 | 11/2008 | Martzel |
| 2008/0302374 A1 | 12/2008 | Wengert et al. |
| 2009/0082647 A1* | 3/2009 | Busby .............. A61B 5/150503 600/309 |
| 2009/0095311 A1 | 4/2009 | Hon |
| 2009/0095312 A1 | 4/2009 | Herbrich et al. |
| 2009/0126745 A1 | 5/2009 | Hon |
| 2009/0188490 A1 | 7/2009 | Hon |
| 2009/0230117 A1 | 9/2009 | Fernando et al. |
| 2009/0267622 A1* | 10/2009 | Hansen ............. B60R 21/01532 324/684 |
| 2009/0272379 A1 | 11/2009 | Thorens et al. |
| 2009/0283103 A1 | 11/2009 | Nielsen et al. |
| 2009/0320863 A1 | 12/2009 | Fernando et al. |
| 2010/0043809 A1 | 2/2010 | Magnon |
| 2010/0083959 A1 | 4/2010 | Siller |
| 2010/0200006 A1 | 8/2010 | Robinson et al. |
| 2010/0229881 A1 | 9/2010 | Hearn |
| 2010/0242974 A1 | 9/2010 | Pan |
| 2010/0307518 A1 | 12/2010 | Wang |
| 2010/0313901 A1 | 12/2010 | Fernando et al. |
| 2011/0005535 A1 | 1/2011 | Xiu |
| 2011/0011396 A1 | 1/2011 | Fang |
| 2011/0036363 A1 | 2/2011 | Urtsev et al. |
| 2011/0036365 A1 | 2/2011 | Chong et al. |
| 2011/0094523 A1 | 4/2011 | Thorens et al. |
| 2011/0126848 A1 | 6/2011 | Zuber et al. |
| 2011/0155153 A1 | 6/2011 | Thorens et al. |
| 2011/0155718 A1 | 6/2011 | Greim et al. |
| 2011/0168194 A1 | 7/2011 | Hon |
| 2011/0265806 A1 | 11/2011 | Alarcon et al. |
| 2011/0288685 A1* | 11/2011 | Usem ...................... G07F 17/12 700/275 |
| 2011/0309157 A1 | 12/2011 | Yang et al. |
| 2012/0042885 A1 | 2/2012 | Stone et al. |
| 2012/0060853 A1 | 3/2012 | Robinson et al. |
| 2012/0111347 A1 | 5/2012 | Hon |
| 2012/0132643 A1 | 5/2012 | Choi et al. |
| 2012/0227752 A1 | 9/2012 | Alelov |
| 2012/0231464 A1 | 9/2012 | Yu et al. |
| 2012/0260927 A1 | 10/2012 | Liu |
| 2012/0279512 A1 | 11/2012 | Hon |
| 2012/0294876 A1* | 11/2012 | Zimmerman .......... A61B 5/082 424/184.1 |
| 2012/0318882 A1* | 12/2012 | Abehasera ............ A61M 11/041 239/1 |
| 2013/0037041 A1 | 2/2013 | Worm et al. |
| 2013/0056013 A1 | 3/2013 | Terry et al. |
| 2013/0081625 A1 | 4/2013 | Rustad et al. |
| 2013/0081642 A1 | 4/2013 | Safari |
| 2013/0104916 A1* | 5/2013 | Bellinger .............. A61M 15/06 131/328 |
| 2013/0192619 A1 | 8/2013 | Tucker et al. |
| 2013/0220315 A1* | 8/2013 | Conley ................ A24F 47/008 128/202.21 |
| 2013/0255702 A1* | 10/2013 | Griffith, Jr. ........... A24F 47/008 131/328 |
| 2013/0284192 A1* | 10/2013 | Peleg ................... A24F 47/002 131/329 |
| 2013/0306084 A1 | 11/2013 | Flick |
| 2013/0319439 A1 | 12/2013 | Gorelick et al. |
| 2013/0340750 A1 | 12/2013 | Thorens et al. |
| 2013/0340775 A1 | 12/2013 | Juster et al. |
| 2014/0000638 A1 | 1/2014 | Sebastian et al. |
| 2014/0060554 A1 | 3/2014 | Collett et al. |
| 2014/0060555 A1 | 3/2014 | Chang et al. |
| 2014/0096781 A1 | 4/2014 | Sears et al. |
| 2014/0096782 A1 | 4/2014 | Ampolini et al. |
| 2014/0107815 A1* | 4/2014 | LaMothe ................ A24F 15/18 700/90 |
| 2014/0109921 A1 | 4/2014 | Chen |
| 2014/0157583 A1 | 6/2014 | Ward et al. |
| 2014/0209105 A1* | 7/2014 | Sears ..................... A24F 47/008 131/328 |
| 2014/0253144 A1 | 9/2014 | Novak et al. |
| 2014/0261408 A1 | 9/2014 | DePiano et al. |
| 2014/0261486 A1 | 9/2014 | Potter et al. |
| 2014/0261487 A1 | 9/2014 | Chapman et al. |
| 2014/0261495 A1 | 9/2014 | Novak et al. |
| 2014/0270727 A1 | 9/2014 | Ampolini et al. |
| 2014/0270729 A1 | 9/2014 | DePiano et al. |
| 2014/0270730 A1 | 9/2014 | DePiano et al. |
| 2014/0345631 A1 | 11/2014 | Bowen et al. |
| 2015/0053217 A1* | 2/2015 | Steingraber ........... A24F 47/008 131/329 |
| 2015/0181945 A1* | 7/2015 | Tremblay ................ A24F 40/53 131/328 |
| 2015/0201674 A1 | 7/2015 | Dooly et al. |
| 2015/0211915 A1* | 7/2015 | Scarlett ................. G01F 23/268 73/304 C |
| 2015/0297779 A1* | 10/2015 | Conroy ................. B05B 7/2416 239/1 |
| 2015/0313282 A1 | 11/2015 | Ademe et al. |
| 2015/0335074 A1* | 11/2015 | Leung .................. A61M 11/044 131/328 |
| 2016/0106936 A1* | 4/2016 | Kimmel ................ A24F 47/008 128/202.21 |
| 2016/0150824 A1* | 6/2016 | Memari ................ H02J 7/0042 131/329 |
| 2016/0206000 A1* | 7/2016 | Lord ....................... A24F 40/53 |
| 2016/0219933 A1* | 8/2016 | Henry, Jr. ............. A24F 47/008 |
| 2016/0302488 A1* | 10/2016 | Fernando ............. A24F 47/008 |
| 2016/0331030 A1* | 11/2016 | Ampolini ............. A24F 47/008 |
| 2016/0345628 A1* | 12/2016 | Sabet ....................... A24F 15/18 |
| 2016/0366939 A1* | 12/2016 | Alarcon ................ G01F 1/6888 |
| 2017/0064996 A1* | 3/2017 | Mironov ................ A24F 47/008 |
| 2017/0318861 A1* | 11/2017 | Thorens ................ A24F 47/008 |

FOREIGN PATENT DOCUMENTS

| | | |
|---|---|---|
| CN | 1541577 | 11/2004 |
| CN | 2719043 | 8/2005 |
| CN | 200997909 | 1/2008 |
| CN | 101116542 | 2/2008 |
| CN | 101176805 | 5/2008 |
| CN | 201379072 | 1/2010 |
| DE | 10 2006 004 484 | 8/2007 |
| DE | 102006041042 | 3/2008 |
| DE | 20 2009 010 400 | 11/2009 |
| EP | 0 295 122 | 12/1988 |
| EP | 0 430 566 | 6/1991 |
| EP | 0503767 B1 | 5/1995 |
| EP | 0 845 220 | 6/1998 |
| EP | 1 618 803 | 1/2006 |
| EP | 2 316 286 | 5/2011 |
| EP | 2468117 A1 | 6/2012 |
| GB | 2469850 | 11/2010 |
| KR | 100193885 B1 | 6/1999 |
| RU | 103281 U1 | 4/2011 |
| WO | WO 1997/48293 | 12/1997 |
| WO | WO 2003/034847 | 5/2003 |
| WO | WO 2004/043175 | 5/2004 |
| WO | WO 2004/080216 | 9/2004 |
| WO | WO 2005/099494 | 10/2005 |
| WO | WO 2007/078273 | 7/2007 |
| WO | WO 2007/131449 | 11/2007 |
| WO | WO 2009/105919 | 9/2009 |
| WO | WO 2009/155734 | 12/2009 |
| WO | WO 2010/003480 | 1/2010 |
| WO | WO 2010/045670 | 4/2010 |
| WO | WO 2010/073122 | 7/2010 |
| WO | WO 2010/118644 | 10/2010 |
| WO | WO 2010/140937 | 12/2010 |
| WO | WO 2011/010334 | 1/2011 |
| WO | WO 2012/072762 | 6/2012 |
| WO | WO 2012/100523 | 8/2012 |

(56) References Cited

FOREIGN PATENT DOCUMENTS

| | | |
|---|---|---|
| WO | WO 2013/089551 | 6/2013 |
| WO | 2013186688 A1 | 12/2013 |
| WO | 2014150704 A2 | 9/2014 |
| WO | 2015082560 A1 | 6/2015 |
| WO | 2015127429 A1 | 8/2015 |
| WO | 2017045897 A1 | 3/2017 |

OTHER PUBLICATIONS

Partial International Search Report for International Application No. PCT/IB2016/057734 dated Mar. 3, 2017.

\* cited by examiner

PROXIMITY SENSING FOR AN AEROSOL DELIVERY DEVICE

TECHNOLOGICAL FIELD

The present disclosure relates to aerosol delivery devices such as smoking articles, and more particularly to aerosol delivery devices that may utilize electrically generated heat for the production of aerosol (e.g., smoking articles commonly referred to as electronic cigarettes). The smoking articles may be configured to heat an aerosol precursor, which may incorporate materials that may be made or derived from, or otherwise incorporate tobacco, the precursor being capable of forming an inhalable substance for human consumption.

BACKGROUND

Many smoking devices have been proposed through the years as improvements upon, or alternatives to, smoking products that require combusting tobacco for use. Many of those devices purportedly have been designed to provide the sensations associated with cigarette, cigar or pipe smoking, but without delivering considerable quantities of incomplete combustion and pyrolysis products that result from the burning of tobacco. To this end, there have been proposed numerous smoking products, flavor generators and medicinal inhalers that utilize electrical energy to vaporize or heat a volatile material, or attempt to provide the sensations of cigarette, cigar or pipe smoking without burning tobacco to a significant degree. See, for example, the various alternative smoking articles, aerosol delivery devices and heat generating sources set forth in the background art described in U.S. Pat. No. 7,726,320 to Robinson et al. and U.S. Pat. No. 8,881,737 to Collett et al., which are incorporated herein by reference. See also, for example, the various types of smoking articles, aerosol delivery devices and electrically-powered heat generating sources referenced by brand name and commercial source in U.S. Pat. Pub. No. 2015/0216232 to Bless et al., which is incorporated herein by reference. Additionally, various types of electrically powered aerosol and vapor delivery devices also have been proposed in U.S. Pat. Pub. Nos. 2014/0096781 to Sears et al. and 2014/0283859 to Minskoff et al., as well as U.S. patent application Ser. No. 14/282,768 to Sears et al., filed May 20, 2014; Ser. No. 14/286,552 to Brinkley et al., filed May 23, 2014; Ser. No. 14/327,776 to Ampolini et al., filed Jul. 10, 2014; and Ser. No. 14/465,167 to Worm et al., filed Aug. 21, 2014; all of which are incorporated herein by reference.

BRIEF SUMMARY

The present disclosure relates to aerosol delivery devices, methods of forming such devices, and elements of such devices. The present disclosure includes, without limitation, the following example implementations. In some example implementations, a control body is provided. The control body is coupled or coupleable with a cartridge that is equipped with a heating element and contains an aerosol precursor composition, the control body being coupled or coupleable with the cartridge to form an aerosol delivery device in which the heating element is configured to activate and vaporize components of the aerosol precursor composition. The control body comprises a housing; and within the housing, a control component configured to operate in an active mode in which the control body is coupled with the cartridge, the control component in the active mode being configured to control the heating element to activate and vaporize components of the aerosol precursor composition; and a proximity sensor configured to detect a presence of an object nearby the control body without requiring any physical contact with the object, the proximity sensor or control component being further configured to control operation of at least one functional element of the aerosol delivery device in response to the presence of the object so detected.

In some example implementations of the control body of the preceding or any subsequent example implementation, or any combination thereof, the proximity sensor is an inductive, capacitive, ultrasonic, Hall effect, photoelectric or non-mechanical magnetic proximity sensor.

In some example implementations of the control body of any preceding or any subsequent example implementation, or any combination thereof, the proximity sensor is configured to detect the presence of the object within a range that is user-programmable.

In some example implementations of the control body of any preceding or any subsequent example implementation, or any combination thereof, the proximity sensor being configured to detect the presence of the object includes being configured to obtain a measurement and detect the presence of the object in an instance in which the measurement satisfies a threshold, and wherein the threshold is user-programmable to depend on a specific user such that the proximity sensor is configured to detect the presence of the specific user.

In some example implementations of the control body of any preceding or any subsequent example implementation, or any combination thereof, the operation of the at least one functional element is user-programmable.

In some example implementations of the control body of any preceding or any subsequent example implementation, or any combination thereof, the proximity sensor or control component being configured to control at least one functional element includes being configured to control a sensory-feedback member to provide a user-perceptible feedback.

In some example implementations of the control body of any preceding or any subsequent example implementation, or any combination thereof, the proximity sensor or control component being configured to control at least one functional element includes being configured to alter a power state of the at least one functional element.

In some example implementations of the control body of any preceding or any subsequent example implementation, or any combination thereof, the proximity sensor or control component being configured to alter the power state includes being configured to alter the power state of a communication interface that is coupled to the control component and configured to enable wireless communication.

In some example implementations of the control body of any preceding or any subsequent example implementation, or any combination thereof, the proximity sensor or control component being configured to control at least one functional element includes being configured to control at least one functional element to alter a locked state of the aerosol delivery device.

In some example implementations of the control body of any preceding or any subsequent example implementation, or any combination thereof, the proximity sensor is further configured to output a proximity-detected signal in response to the presence of the object so detected, wherein the control body further comprises a flow sensor configured to detect a flow of air through at least a portion of the housing, and output an airflow-detected signal in response to the flow of air so detected, and wherein the proximity sensor or control component being configured to control operation of at least one functional element includes the control component being configured to initiate operation in the active mode in response to both the proximity-detected signal and airflow-detected signal, and therein control the heating element to activate and vaporize components of the aerosol precursor composition.

In some example implementations of the control body of any preceding or any subsequent example implementation, or any combination thereof, the proximity sensor includes first and second capacitive proximity sensors configured to measure respectively first and second capacitances that indicate respectively the presence of a user and a reference, wherein the proximity sensor is further configured to calculate a level of perspiration of the user from the first and second capacitances, or output or output signals corresponding to the first and second capacitances for the control component to calculate the level of perspiration of the user from the first and second capacitances, and wherein proximity sensor or control component being further configured to control operation of at least one functional element includes being further configured to control operation of at least one functional element in response to the presence and level of perspiration of the user.

In some example implementations of the control body of any preceding or any subsequent example implementation, or any combination thereof, the proximity sensor or control component being configured to control at least one functional element includes being configured to upload to a service platform, data associated with the presence of the object detected by the proximity sensor.

In some example implementations, a cartridge is provided. The cartridge is coupled or coupleable with a control body that is equipped with a control component, the control body being coupled or coupleable with the cartridge to form an aerosol delivery device. The cartridge comprises a housing defining a reservoir configured to retain aerosol precursor composition; a heating element configured to operate in an active mode in which the cartridge is coupled with the control body, the heating element in the active mode being controllable by the control component to activate and vaporize components of the aerosol precursor composition; and a proximity sensor configured to detect a level of the aerosol precursor composition in the reservoir without requiring any physical contact with the aerosol precursor composition, the proximity sensor or control component being configured to control operation of at least one functional element of the aerosol delivery device in response to the level of the aerosol precursor composition so detected.

In some example implementations of the cartridge of the preceding or any subsequent example implementation, or any combination thereof, the proximity sensor is a capacitive, ultrasonic, Hall effect, photoelectric or non-mechanical magnetic proximity sensor.

In some example implementations of the cartridge of any preceding or any subsequent example implementation, or any combination thereof, the proximity sensor includes first and second capacitive proximity sensors configured to measure respectively first and second capacitances that indicate respectively a level and a reference, and the proximity sensor being configured to detect the level of the aerosol precursor composition includes being configured to calculate the level of the aerosol precursor composition from the first and second capacitances, or output or output signals corresponding to the first and second capacitances for the control component to calculate the level of the aerosol precursor composition from the first and second capacitances.

In some example implementations of the cartridge of any preceding or any subsequent example implementation, or any combination thereof, the proximity sensor or control component being configured to control at least one functional element includes being configured to control a sensory-feedback member to provide a user-perceptible feedback.

In some example implementations of the cartridge of any preceding or any subsequent example implementation, or any combination thereof, the proximity sensor or control component being configured to control at least one functional element includes being configured to control at least one functional element to alter a locked state of the aerosol delivery device.

In some example implementations of the cartridge of any preceding or any subsequent example implementation, or any combination thereof, the proximity sensor or control component being configured to control at least one functional element includes being configured to upload to a service platform, data associated with the level of the aerosol precursor composition detected by the proximity sensor.

These and other features, aspects, and advantages of the present disclosure will be apparent from a reading of the following detailed description together with the accompanying drawings, which are briefly described below. The present disclosure includes any combination of two, three, four or more features or elements set forth in this disclosure, regardless of whether such features or elements are expressly combined or otherwise recited in a specific example implementation described herein. This disclosure is intended to be read holistically such that any separable features or elements of the disclosure, in any of its aspects and example implementations, should be viewed as intended, namely to be combinable, unless the context of the disclosure clearly dictates otherwise.

It will therefore be appreciated that this Brief Summary is provided merely for purposes of summarizing some example implementations so as to provide a basic understanding of some aspects of the disclosure. Accordingly, it will be appreciated that the above described example implementations are merely examples and should not be construed to narrow the scope or spirit of the disclosure in any way. Other example implementations, aspects and advantages will become apparent from the following detailed description taken in conjunction with the accompanying drawings which illustrate, by way of example, the principles of some described example implementations.

BRIEF DESCRIPTION OF THE DRAWING(S)

Having thus described the disclosure in the foregoing general terms, reference will now be made to the accompanying drawings, which are not necessarily drawn to scale, and wherein:

DETAILED DESCRIPTION

The present disclosure will now be described more fully hereinafter with reference to example implementations thereof. These example implementations are described so that this disclosure will be thorough and complete, and will fully convey the scope of the disclosure to those skilled in the art. Indeed, the disclosure may be embodied in many different forms and should not be construed as limited to the implementations set forth herein; rather, these implementations are provided so that this disclosure will satisfy applicable legal requirements. As used in the specification and the appended claims, the singular forms "a," "an," "the" and the like include plural referents unless the context clearly dictates otherwise.

As described hereinafter, example implementations of the present disclosure relate to aerosol delivery systems. Aerosol delivery systems according to the present disclosure use electrical energy to heat a material (preferably without combusting the material to any significant degree) to form an inhalable substance; and components of such systems have the form of articles most preferably are sufficiently compact to be considered hand-held devices. That is, use of components of preferred aerosol delivery systems does not result in the production of smoke in the sense that aerosol results principally from by-products of combustion or pyrolysis of tobacco, but rather, use of those preferred systems results in the production of vapors resulting from volatilization or vaporization of certain components incorporated therein. In some example implementations, components of aerosol delivery systems may be characterized as electronic cigarettes, and those electronic cigarettes most preferably incorporate tobacco and/or components derived from tobacco, and hence deliver tobacco derived components in aerosol form.

Aerosol generating pieces of certain preferred aerosol delivery systems may provide many of the sensations (e.g., inhalation and exhalation rituals, types of tastes or flavors, organoleptic effects, physical feel, use rituals, visual cues such as those provided by visible aerosol, and the like) of smoking a cigarette, cigar or pipe that is employed by lighting and burning tobacco (and hence inhaling tobacco smoke), without any substantial degree of combustion of any component thereof. For example, the user of an aerosol generating piece of the present disclosure can hold and use that piece much like a smoker employs a traditional type of smoking article, draw on one end of that piece for inhalation of aerosol produced by that piece, take or draw puffs at selected intervals of time, and the like.

Aerosol delivery systems of the present disclosure also can be characterized as being vapor-producing articles or medicament delivery articles. Thus, such articles or devices can be adapted so as to provide one or more substances (e.g., flavors and/or pharmaceutical active ingredients) in an inhalable form or state. For example, inhalable substances can be substantially in the form of a vapor (i.e., a substance that is in the gas phase at a temperature lower than its critical point). Alternatively, inhalable substances can be in the form of an aerosol (i.e., a suspension of fine solid particles or liquid droplets in a gas). For purposes of simplicity, the term "aerosol" as used herein is meant to include vapors, gases and aerosols of a form or type suitable for human inhalation, whether or not visible, and whether or not of a form that might be considered to be smoke-like.

Aerosol delivery systems of the present disclosure generally include a number of components provided within an outer body or shell, which may be referred to as a housing. The overall design of the outer body or shell can vary, and the format or configuration of the outer body that can define the overall size and shape of the aerosol delivery device can vary. Typically, an elongated body resembling the shape of a cigarette or cigar can be a formed from a single, unitary housing or the elongated housing can be formed of two or more separable bodies. For example, an aerosol delivery device can comprise an elongated shell or body that can be substantially tubular in shape and, as such, resemble the shape of a conventional cigarette or cigar. In one example, all of the components of the aerosol delivery device are contained within one housing. Alternatively, an aerosol delivery device can comprise two or more housings that are joined and are separable. For example, an aerosol delivery device can possess at one end a control body comprising a housing containing one or more reusable components (e.g., an accumulator such as a rechargeable battery and/or supercapacitor, and various electronics for controlling the operation of that article), and at the other end and removably coupleable thereto, an outer body or shell containing a disposable portion (e.g., a disposable flavor-containing cartridge).

Aerosol delivery systems of the present disclosure most preferably comprise some combination of a power source (i.e., an electrical power source), at least one control component (e.g., means for actuating, controlling, regulating and ceasing power for heat generation, such as by controlling electrical current flow the power source to other components of the article—e.g., a microprocessor, individually or as part of a microcontroller), a heater or heat generation member (e.g., an electrical resistance heating element or other component, which alone or in combination with one or more further elements may be commonly referred to as an "atomizer"), an aerosol precursor composition (e.g., commonly a liquid capable of yielding an aerosol upon application of sufficient heat, such as ingredients commonly referred to as "smoke juice," "e-liquid" and "e-juice"), and a mouthend region or tip for allowing draw upon the aerosol delivery device for aerosol inhalation (e.g., a defined airflow path through the article such that aerosol generated can be withdrawn therefrom upon draw).

More specific formats, configurations and arrangements of components within the aerosol delivery systems of the present disclosure will be evident in light of the further disclosure provided hereinafter. Additionally, the selection and arrangement of various aerosol delivery system components can be appreciated upon consideration of the commercially available electronic aerosol delivery devices, such as those representative products referenced in background art section of the present disclosure.

In various examples, an aerosol delivery device can comprise a reservoir configured to retain the aerosol precursor composition. The reservoir particularly can be formed of a porous material (e.g., a fibrous material) and thus may be referred to as a porous substrate (e.g., a fibrous substrate).

A fibrous substrate useful as a reservoir in an aerosol delivery device can be a woven or nonwoven material formed of a plurality of fibers or filaments and can be formed of one or both of natural fibers and synthetic fibers. For example, a fibrous substrate may comprise a fiberglass material. In particular examples, a cellulose acetate material can be used. In other example implementations, a carbon material can be used. A reservoir may be substantially in the form of a container and may include a fibrous material included therein.

Figure 1:
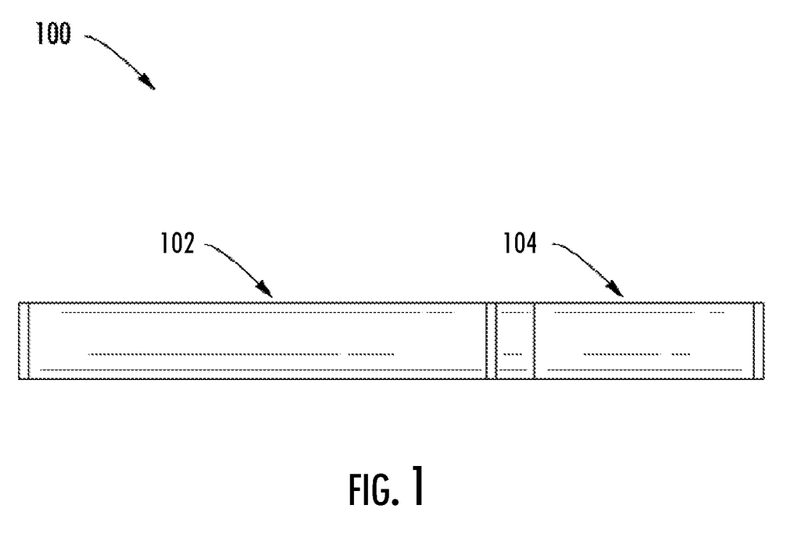
FIG. 1 illustrates a side view of an aerosol delivery device including a cartridge coupled to a control body according to an example implementation of the present disclosure.

FIG. 1 illustrates a side view of an aerosol delivery device 100 including a control body 102 and a cartridge 104, according to various example implementations of the present disclosure. In particular, FIG. 1 illustrates the control body and the cartridge coupled to one another. The control body and the cartridge may be detachably aligned in a functioning relationship. Various mechanisms may connect the cartridge to the control body to result in a threaded engagement, a press-fit engagement, an interference fit, a magnetic engagement or the like. The aerosol delivery device may be substantially rod-like, substantially tubular shaped, or substantially cylindrically shaped in some example implementations when the cartridge and the control body are in an assembled configuration. The aerosol delivery device may also be substantially rectangular or rhomboidal in cross-section, which may lend itself to greater compatibility with a substantially flat or thin-film power source, such as a power source including a flat battery. The cartridge and control body may include separate, respective housings or outer bodies, which may be formed of any of a number of different materials. The housing may be formed of any suitable, structurally-sound material. In some examples, the housing may be formed of a metal or alloy, such as stainless steel, aluminum or the like. Other suitable materials include various plastics (e.g., polycarbonate), metal-plating over plastic, ceramics and the like.

In some example implementations, one or both of the control body 102 or the cartridge 104 of the aerosol delivery device 100 may be referred to as being disposable or as being reusable. For example, the control body may have a replaceable battery or a rechargeable battery and thus may be combined with any type of recharging technology, including connection to a typical wall charger, connection to a car charger (i.e., a cigarette lighter receptacle), connection to a computer, such as through a universal serial bus (USB) cable or connector, connection to a photovoltaic cell (sometimes referred to as a solar cell) or solar panel of solar cells, or connection to a RF-to-DC converter. Further, in some example implementations, the cartridge may comprise a single-use cartridge, as disclosed in U.S. Pat. No. 8,910,639 to Chang et al., which is incorporated herein by reference in its entirety.

Figure 2:
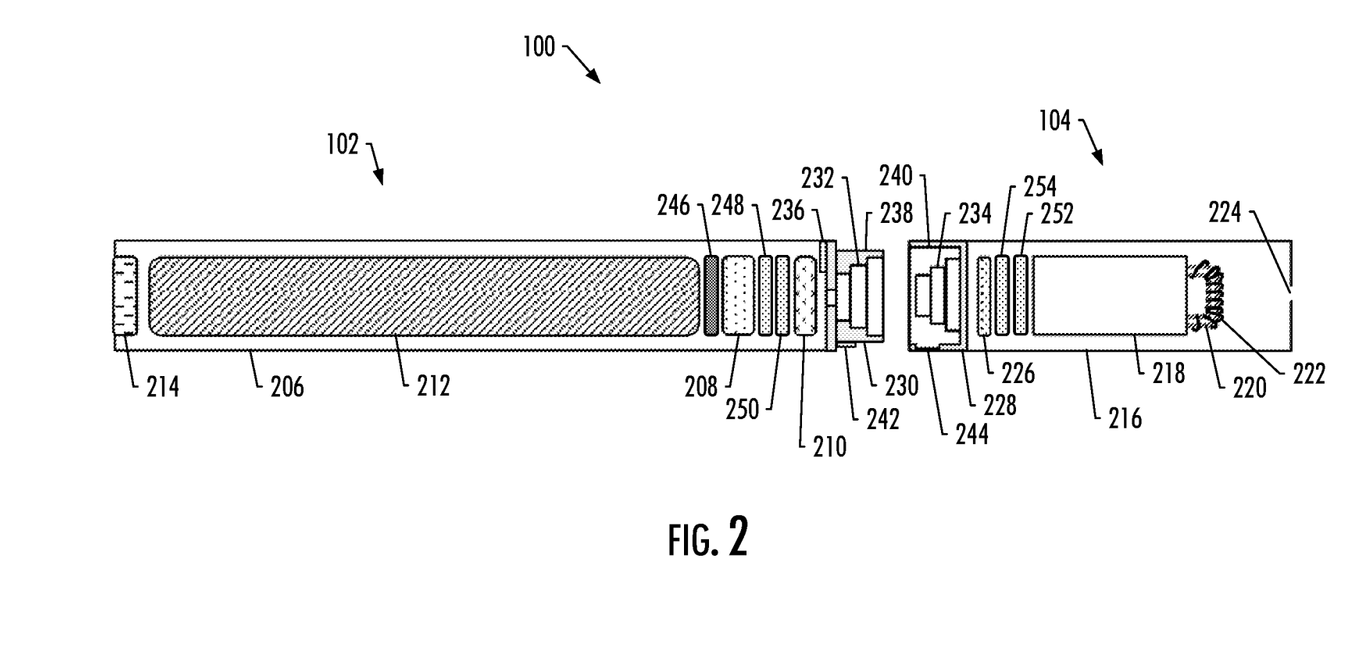
FIG. 2 is a partially cut-away view of the aerosol delivery device according to various example implementations.

FIG. 2 more particularly illustrates the aerosol delivery device 100, in accordance with some example implementations. As seen in the cut-away view illustrated therein, again, the aerosol delivery device can comprise a control body 102 and a cartridge 104 each of which include a number of respective components. The components illustrated in FIG. 2 are representative of the components that may be present in a control body and cartridge and are not intended to limit the scope of components that are encompassed by the present disclosure. As shown, for example, the control body can be formed of a control body shell 206 that can include a control component 208 (e.g., a microprocessor, individually or as part of a microcontroller), a flow sensor 210, a power source 212 and one or more light-emitting diodes (LEDs) 214, and such components can be variably aligned. The power source may include, for example, a battery (single-use or rechargeable), solid-state battery, thin-film solid-state battery, supercapacitor or the like, or some combination thereof. Some examples of a suitable power source are provided in U.S. patent application Ser. No. 14/918,926 to Sur et al., filed Oct. 21, 2015, which is incorporated by reference. The LED may be one example of a suitable visual indicator with which the aerosol delivery device 100 may be equipped. Other indicators such as audio indicators (e.g., speakers), haptic indicators (e.g., vibration motors) or the like can be included in addition to or as an alternative to visual indicators such as the LED.

The cartridge 104 can be formed of a cartridge shell 216 enclosing a reservoir 218 configured to retain the aerosol precursor composition, and including a heater 222 (sometimes referred to as a heating element). In various configurations, this structure may be referred to as a tank; and accordingly, the terms "cartridge," "tank" and the like may be used interchangeably to refer to a shell or other housing enclosing a reservoir for aerosol precursor composition, and including a heater.

As shown, in some examples, the reservoir 218 may be in fluid communication with a liquid transport element 220 adapted to wick or otherwise transport an aerosol precursor composition stored in the reservoir housing to the heater 222. In some examples, a valve may be positioned between the reservoir and heater, and configured to control an amount of aerosol precursor composition passed or delivered from the reservoir to the heater.

Various examples of materials configured to produce heat when electrical current is applied therethrough may be employed to form the heater 222. The heater in these examples may be a resistive heating element such as a wire coil, micro heater or the like. Example materials from which the heating element may be formed include Kanthal (FeCrAl), Nichrome, stainless steel, Molybdenum disilicide ($MoSi_2$), molybdenum silicide (MoSi), Molybdenum disilicide doped with Aluminum ($Mo(Si,Al)_2$), graphite and graphite-based materials (e.g., carbon-based foams and yarns) and ceramics (e.g., positive or negative temperature coefficient ceramics). Example implementations of heaters or heating members useful in aerosol delivery devices according to the present disclosure are further described below, and can be incorporated into devices such as illustrated in FIG. 2 as described herein.

An opening 224 may be present in the cartridge shell 216 (e.g., at the mouthend) to allow for egress of formed aerosol from the cartridge 104.

The cartridge 104 also may include one or more electronic components 226, which may include an integrated circuit, a memory component, a sensor, or the like. The electronic components may be adapted to communicate with the control component 208 and/or with an external device by wired or wireless means. The electronic components may be positioned anywhere within the cartridge or a base 228 thereof.

Although the control component 208 and the flow sensor 210 are illustrated separately, it is understood that the control component and the flow sensor may be combined as an electronic circuit board with the air flow sensor attached directly thereto. Further, the electronic circuit board may be positioned horizontally relative the illustration of FIG. 1 in that the electronic circuit board can be lengthwise parallel to the central axis of the control body. In some examples, the air flow sensor may comprise its own circuit board or other base element to which it can be attached. In some examples, a flexible circuit board may be utilized. A flexible circuit board may be configured into a variety of shapes, include substantially tubular shapes. In some examples, a flexible circuit board may be combined with, layered onto, or form part or all of a heater substrate as further described below.

The control body 102 and the cartridge 104 may include components adapted to facilitate a fluid engagement therebetween. As illustrated in FIG. 2, the control body can include a coupler 230 having a cavity 232 therein. The base 228 of the cartridge can be adapted to engage the coupler and can include a projection 234 adapted to fit within the cavity. Such engagement can facilitate a stable connection between the control body and the cartridge as well as establish an electrical connection between the power source 212 and control component 208 in the control body and the heater 222 in the cartridge. Further, the control body shell 206 can include an air intake 236, which may be a notch in the shell where it connects to the coupler that allows for passage of ambient air around the coupler and into the shell where it then passes through the cavity 232 of the coupler and into the cartridge through the projection 234.

A coupler and a base useful according to the present disclosure are described in U.S. Pat. App. Pub. No. 2014/0261495 to Novak et al., which is incorporated herein by reference in its entirety. For example, the coupler 230 as seen in FIG. 2 may define an outer periphery 238 configured to mate with an inner periphery 240 of the base 228. In one example the inner periphery of the base may define a radius that is substantially equal to, or slightly greater than, a radius of the outer periphery of the coupler. Further, the coupler may define one or more protrusions 242 at the outer periphery configured to engage one or more recesses 244 defined at the inner periphery of the base. However, various other examples of structures, shapes and components may be employed to couple the base to the coupler. In some examples the connection between the base of the cartridge 104 and the coupler of the control body 102 may be substantially permanent, whereas in other examples the connection therebetween may be releasable such that, for example, the control body may be reused with one or more additional cartridges that may be disposable and/or refillable.

The aerosol delivery device 100 may be substantially rod-like or substantially tubular shaped or substantially cylindrically shaped in some examples. In other examples, further shapes and dimensions are encompassed—e.g., a rectangular or triangular cross-section, multifaceted shapes, or the like.

The reservoir 218 illustrated in FIG. 2 can be a container or can be a fibrous reservoir, as presently described. For example, the reservoir can comprise one or more layers of nonwoven fibers substantially formed into the shape of a tube encircling the interior of the cartridge shell 216, in this example. An aerosol precursor composition can be retained in the reservoir. Liquid components, for example, can be sorptively retained by the reservoir. The reservoir can be in fluid connection with the liquid transport element 220. The liquid transport element can transport the aerosol precursor composition stored in the reservoir via capillary action to the heater 222 that is in the form of a metal wire coil in this example. As such, the heater is in a heating arrangement with the liquid transport element. Example implementations of reservoirs and transport elements useful in aerosol delivery devices according to the present disclosure are further described below, and such reservoirs and/or transport elements can be incorporated into devices such as illustrated in FIG. 2 as described herein. In particular, specific combinations of heating members and transport elements as further described below may be incorporated into devices such as illustrated in FIG. 2 as described herein.

In use, when a user draws on the aerosol delivery device 100, airflow is detected by the flow sensor 210, and the heater 222 is activated to vaporize components of the aerosol precursor composition. Drawing upon the mouthend of the aerosol delivery device causes ambient air to enter the air intake 236 and pass through the cavity 232 in the coupler 230 and the central opening in the projection 234 of the base 228. In the cartridge 104, the drawn air combines with the formed vapor to form an aerosol. The aerosol is whisked, aspirated or otherwise drawn away from the heater and out the opening 224 in the mouthend of the aerosol delivery device.

In some examples, the aerosol delivery device 100 may include a number of additional software-controlled functions. For example, the aerosol delivery device may include a power-source protection circuit configured to detect power-source input, loads on the power-source terminals, and charging input. The power-source protection circuit may include short-circuit protection, under-voltage lock out and/or over-voltage charge protection. The aerosol delivery device may also include components for ambient temperature measurement, and its control component 208 may be configured to control at least one functional element to inhibit power-source charging—particularly of any battery—if the ambient temperature is below a certain temperature (e.g., 0° C.) or above a certain temperature (e.g., 45° C.) prior to start of charging or during charging.

Power delivery from the power source 212 may vary over the course of each puff on the device 100 according to a power control mechanism. The device may include a "long puff" safety timer such that in the event that a user or component failure (e.g., flow sensor 210) causes the device to attempt to puff continuously, the control component 208 may control at least one functional element to terminate the puff automatically after some period of time (e.g., four seconds). Further, the time between puffs on the device may be restricted to less than a period of time (e.g., 100 seconds). A watchdog safety timer may automatically reset the aerosol delivery device if its control component or software running on it becomes unstable and does not service the timer within an appropriate time interval (e.g., eight seconds). Further safety protection may be provided in the event of a defective or otherwise failed flow sensor 210, such as by permanently disabling the aerosol delivery device in order to prevent inadvertent heating. A puffing limit switch may deactivate the device in the event of a pressure sensor fail causing the device to continuously activate without stopping after the four second maximum puff time.

The aerosol delivery device 100 may include a puff tracking algorithm configured for heater lockout once a defined number of puffs has been achieved for an attached cartridge (based on the number of available puffs calculated in light of the e-liquid charge in the cartridge). The aerosol delivery device may include a sleep, standby or low-power mode function whereby power delivery may be automatically cut off after a defined period of non-use. Further safety protection may be provided in that all charge/discharge cycles of the power source 212 may be monitored by the control component 208 over its lifetime. After the power source has attained the equivalent of a predetermined number (e.g., 200) of full discharge and full recharge cycles, it may be declared depleted, and the control component may control at least one functional element to prevent further charging of the power source.

The various components of an aerosol delivery device according to the present disclosure can be chosen from components described in the art and commercially available. Examples of batteries that can be used according to the disclosure are described in U.S. Pat. App. Pub. No. 2010/0028766 to Peckerar et al., which is incorporated herein by reference in its entirety.

The aerosol delivery device 100 can incorporate the sensor 210 or another sensor or detector for control of supply of electric power to the heater 222 when aerosol generation is desired (e.g., upon draw during use). As such, for example, there is provided a manner or method of turning off power to the heater when the aerosol delivery device is not be drawn upon during use, and for turning on power to actuate or trigger the generation of heat by the heater during draw. Additional representative types of sensing or detection mechanisms, structure and configuration thereof, components thereof, and general methods of operation thereof, are described in U.S. Pat. No. 5,261,424 to Sprinkel, Jr., U.S. Pat. No. 5,372,148 to McCafferty et al., and PCT Pat. App. Pub. No. WO 2010/003480 to Flick, all of which are incorporated herein by reference in their entireties.

The aerosol delivery device 100 most preferably incorporates the control component 208 or another control mechanism for controlling the amount of electric power to the heater 222 during draw. Representative types of electronic components, structure and configuration thereof, features thereof, and general methods of operation thereof, are described in U.S. Pat. No. 4,735,217 to Gerth et al., U.S. Pat. No. 4,947,874 to Brooks et al., U.S. Pat. No. 5,372,148 to McCafferty et al., U.S. Pat. No. 6,040,560 to Fleischhauer et al., U.S. Pat. No. 7,040,314 to Nguyen et al., U.S. Pat. No. 8,205,622 to Pan, U.S. Pat. App. Pub. No. 2009/0230117 to Fernando et al., U.S. Pat. App. Pub. No. 2014/0060554 to Collet et al., U.S. Pat. App. Pub. No. 2014/0270727 to Ampolini et al., and U.S. patent application Ser. No. 14/209,191 to Henry et al., filed Mar. 13, 2014, all of which are incorporated herein by reference in their entireties.

Representative types of substrates, reservoirs or other components for supporting the aerosol precursor are described in U.S. Pat. No. 8,528,569 to Newton, U.S. Pat. App. Pub. No. 2014/0261487 to Chapman et al., U.S. patent application Ser. No. 14/011,992 to Davis et al., filed Aug. 28, 2013, and U.S. patent application Ser. No. 14/170,838 to Bless et al., filed Feb. 3, 2014, all of which are incorporated herein by reference in their entireties. Additionally, various wicking materials, and the configuration and operation of those wicking materials within certain types of electronic cigarettes, are set forth in U.S. Pat. App. Pub. No. 2014/0209105 to Sears et al., which is incorporated herein by reference in its entirety.

The aerosol precursor composition, also referred to as a vapor precursor composition, may comprise a variety of components including, by way of example, a polyhydric alcohol (e.g., glycerin, propylene glycol or a mixture thereof), nicotine, tobacco, tobacco extract and/or flavorants. Representative types of aerosol precursor components and formulations also are set forth and characterized in U.S. Pat. No. 7,217,320 to Robinson et al. and U.S. Pat. Pub. Nos. 2013/0008457 to Zheng et al.; 2013/0213417 to Chong et al.; 2014/0060554 to Collett et al.; 2015/0020823 to Lipowicz et al.; and 2015/0020830 to Koller, as well as WO 2014/182736 to Bowen et al, the disclosures of which are incorporated herein by reference. Other aerosol precursors that may be employed include the aerosol precursors that have been incorporated in the VUSE® product by R. J. Reynolds Vapor Company, the BLU™ product by Imperial Tobacco Group PLC, the MISTIC MENTHOL product by Mistic Ecigs, and the VYPE product by CN Creative Ltd. Also desirable are the so-called "smoke juices" for electronic cigarettes that have been available from Johnson Creek Enterprises LLC.

Additional representative types of components that yield visual cues or indicators may be employed in the aerosol delivery device 100, such as visual indicators and related components, audio indicators, haptic indicators and the like. Examples of suitable LED components, and the configurations and uses thereof, are described in U.S. Pat. No. 5,154,192 to Sprinkel et al., U.S. Pat. No. 8,499,766 to Newton, U.S. Pat. No. 8,539,959 to Scatterday, and U.S. patent application Ser. No. 14/173,266 to Sears et al., filed Feb. 5, 2014, all of which are incorporated herein by reference in their entireties.

Yet other features, controls or components that can be incorporated into aerosol delivery devices of the present disclosure are described in U.S. Pat. No. 5,967,148 to Harris et al., U.S. Pat. No. 5,934,289 to Watkins et al., U.S. Pat. No. 5,954,979 to Counts et al., U.S. Pat. No. 6,040,560 to Fleischhauer et al., U.S. Pat. No. 8,365,742 to Hon, U.S. Pat. No. 8,402,976 to Fernando et al., U.S. Pat. App. Pub. No. 2005/0016550 to Katase, U.S. Pat. App. Pub. No. 2010/0163063 to Fernando et al., U.S. Pat. App. Pub. No. 2013/0192623 to Tucker et al., U.S. Pat. App. Pub. No. 2013/0298905 to Leven et al., U.S. Pat. App. Pub. No. 2013/0180553 to Kim et al., U.S. Pat. App. Pub. No. 2014/0000638 to Sebastian et al., U.S. Pat. App. Pub. No. 2014/0261495 to Novak et al., and U.S. Pat. App. Pub. No. 2014/0261408 to DePiano et al., all of which are incorporated herein by reference in their entireties.

The control component 208 includes a number of electronic components, and in some examples may be formed of a printed circuit board (PCB) that supports and electrically connects the electronic components. The electronic components may include a microprocessor or processor core, and a memory. In some examples, the control component may include a microcontroller with integrated processor core and memory, and may further include one or more integrated input/output peripherals. In some examples, the control component may be coupled to a communication interface 246 to enable wireless communication with one or more networks, computing devices or other appropriately-enabled devices. Examples of suitable communication interfaces are disclosed in U.S. patent application Ser. No. 14/638,562, filed Mar. 4, 2015, to Marion et al., the content of which is incorporated by reference in its entirety. And examples of suitable manners according to which the aerosol delivery device may be configured to wirelessly communicate are disclosed in U.S. patent application Ser. No. 14/327,776, filed Jul. 10, 2014, to Ampolini et al., and U.S. patent application Ser. No. 14/609,032, filed Jan. 29, 2015, to Henry, Jr. et al., each of which is incorporated herein by reference in its entirety.

In accordance with some example implementations, the control body 102 may include a proximity sensor 248 configured to detect a presence of an object nearby the control body without requiring any physical contact with the object. Examples of a suitable proximity sensor include an inductive, capacitive, ultrasonic, Hall effect, photoelectric or non-mechanical magnetic proximity sensor. One particular example of a suitable proximity sensor includes a capacitive proximity sensor and AD7150 or AD7151 capacitance converter from Analog Devices of Norwood, Mass.

The proximity sensor 248 or control component 208 may be configured to control operation of at least one functional element of the aerosol delivery device 100 in response to the presence of the object so detected. The aerosol delivery device may be configured in any of a number of different manners for any of a number of different applications, and in some examples may be user programmable for different applications. More particularly, in some examples, this user-programmability may extend to the range of the proximity sensor, the operation of the functional element(s) or the like. As another example, the proximity sensor may obtain a measurement and detect the presence of the object in an instance in which the measurement satisfies a threshold, and this threshold may be user-programmable to depend on a specific user such that the proximity sensor is configured to detect the presence of the specific user.

Functional element(s) of the aerosol delivery device 100 may be controlled in any of a number of different manners in response to the presence of the object. For example, a sensory-feedback member 250 (e.g., a LED, auditory element, vibratory element) may be controlled to provide a user-perceptible feedback (e.g., visual, audible, haptic feedback). Additionally or alternatively, the proximity sensor 248 or control component 208 may alter a power state of at least one functional element, such as the communication interface 246. This may include, for example, activation of the communication interface and perhaps other functional elements from a low-power state.

As another example, functional element(s) may be controlled to alter a locked state of the aerosol delivery device 100. This may include, for example, enabling one or more components of the aerosol delivery device for operation when the presence of a user is detected. Similar functionality may also be used to limit active-mode operation of the aerosol delivery device to only those instances in which both the flow sensor 210 detects a flow of air through the aerosol delivery device, and the proximity sensor 248 detects the presence of a user. More particularly, for example, the proximity sensor may output a proximity-detected signal in response to the presence of the object so detected, and the flow sensor may output an airflow-detected signal in response to detection of a flow of air through at least a portion of the aerosol delivery device. The control component 208 may then be configured to initiate operation in the active mode in response to both the proximity-detected signal and airflow-detected signal, and therein control the heating element to activate and vaporize components of the aerosol precursor composition.

In addition to or in lieu of applications involving activation of functional element(s) from a low-power state, or unlocking the aerosol delivery device 100 for active-mode operation, the proximity sensor 248 may enable an even greater number of applications. In some examples, the range of the proximity sensor may be set to enable use of the aerosol delivery device as a warning system. The aerosol delivery device and its proximity sensor may be used to detect the presence of an intruder or wild animal in proximity of the aerosol delivery device's user, and control the sensory-feedback member 250 to provide a user-perceptible feedback to warn the user. In another example, the aerosol delivery device and its proximity sensor may be used to detect the presence of a vehicle, person or other object approaching a moving vehicle carrying the aerosol delivery device's user, and control the sensory-feedback member to provide a user-perceptible feedback to warn the user.

In some examples, the aerosol delivery device 100 with proximity sensor 248 may be used to as a sweat detector to detect perspiration from its user. In the case of a capacitive proximity sensor, the capacitance of a capacitor may depend on relative static permittivity. This relative static permittivity may depend on humidity, which for a capacitor in proximity of a user, may depend on the user's perspiration. The proximity sensor may therefore include one capacitive proximity sensor to measure a capacitance that depends on perspiration of a user, and another proximity sensor to measure a reference capacitance that depends on ambient atmospheric pressure and humidity; and a comparison of the two capacitances may reveal a measure of perspiration of the user.

More particularly, for example, the proximity sensor 248 may include first and second capacitive proximity sensors configured to measure respectively first and second capacitances that indicate respectively the presence of a user and a reference. The proximity sensor may then calculate a level of perspiration of the user from the first and second capacitances, or output or output signals corresponding to the first and second capacitances for the control component 208 to calculate the level of perspiration of the user from the first and second capacitances (e.g., a difference between the first capacitance and second capacitance). The proximity sensor or control component may then control operation of at least one functional element in response to the presence and level of perspiration of the user. This may include, again, control the sensory-feedback member 250 to provide a user-perceptible feedback to warn the user, such as in instances in which the user may be above a threshold level of dehydration (e.g., the difference between capacitances exceeds a threshold level).

As further shown in FIG. 2, in addition to or in lieu of the control body 102, the cartridge may include a proximity sensor 252 and perhaps also a sensory-feedback member 254. Examples of a suitable proximity sensor here include a capacitive, ultrasonic, Hall effect, photoelectric or non-mechanical magnetic proximity sensor. In some examples, this proximity sensor may be configured to detect a level of the aerosol precursor composition in the reservoir 218 without requiring any physical contact with the aerosol precursor composition. The proximity sensor or control component 208, then, may be configured to control operation of functional element(s) of the aerosol delivery device 100 in response to the level of the aerosol precursor composition so detected.

Similar to above with respect to the presence of an object, functional element(s) of the aerosol delivery device 100 may be controlled in any of a number of different manners in response to the level of the aerosol precursor composition. For example, a sensory-feedback member 250, 254 may be controlled to provide a user-perceptible feedback. Additionally or alternatively, for example, functional element(s) may be controlled to alter a locked state of the aerosol delivery device, such as enabling one or more components of the aerosol delivery device for operation when at least a threshold level of aerosol precursor composition is detected.

In any of the foregoing examples, as well as in other examples, the proximity sensor 248, 252 or control component 208 may be configured to upload data associated with the presence of the detected object to a service platform for storage, presentation, analysis or the like. This service platform may include one or more computing devices (e.g., servers), and in some examples, the service platform may provide a cloud computing infrastructure. The aerosol delivery device 100 may communicate with the service platform through its communication interface 246, and possibly one or more networks. This communication may even be less direct with the aerosol delivery device being in communication with a computing device (directly or through one or more networks), which is in turn in communication with the service platform (directly or through one or more networks).

Figure 3:
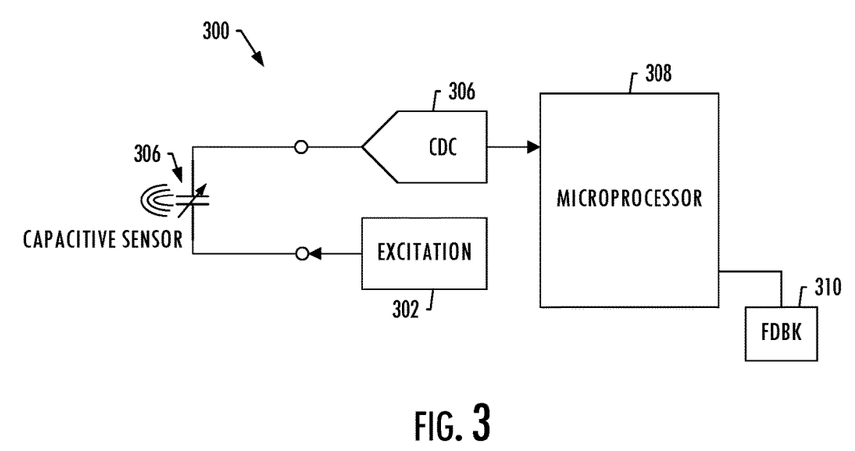
FIGS. 3 and 4 illustrate proximity sensors, according to various example implementations.

FIG. 3 illustrates a proximity sensor 300 that in some examples may correspond to the proximity sensor 248 of FIG. 2. As shown, the proximity sensor may include a source of excitation 302 configured to drive a capacitive proximity sensor 304 configured to measure a change in capacitance in the presence of a nearby object. The measured capacitance may be provided to a capacitance-to-digital converter (CDC) 306 configured to convert the capacitance to a corresponding digital signal. This digital signal may be passed to a microprocessor 308 or other digital processing logic, which may be onboard the proximity sensor or in some examples part of the control component 208. The microprocessor may be in turn configured to control operation of at least one functional element in response to the digital signal and thereby the presence of the detected nearby object. This may include, for example, control of a sensory-feedback member 310, which may also be onboard the proximity sensor or separate from but in communication with the proximity sensor (e.g., sensory-feedback member 250).

Figure 4:
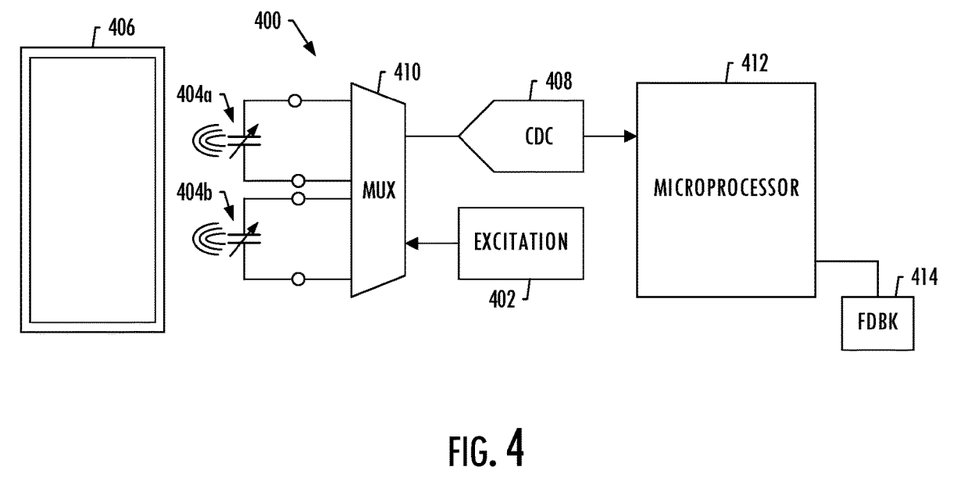

FIG. 4 illustrates a proximity sensor 400 that in some examples may correspond to the proximity sensor 252 of FIG. 2. As shown, the proximity sensor may include a source of excitation 402 configured to drive first and second capacitive proximity sensors 404a, 404b configured to measure respectively first and second capacitances that indicate respectively a level and a reference with respect to aerosol precursor composition in a reservoir 406 (e.g., reservoir 218). The measured capacitances may be provided to a capacitance-to-digital converter (CDC) 408 configured to convert the capacitance to corresponding digital signals. The source of excitation and CDC are shown supporting both capacitive proximity sensors through a multiplexer 410. In another example, the proximity sensor may include a source of excitation and CDC for each of the capacitive proximity sensors.

The digital signals from the CDC 408 may be passed to a microprocessor 412 or other digital processing logic, which may be onboard the proximity sensor 400 or in some examples part of the control component 208. The microprocessor may be in turn configured to calculate the level of the aerosol precursor composition from the digital signals and thereby the first and second capacitances, and control operation of at least one functional element in response to the level of the aerosol precursor composition. This may include, for example, control of a sensory-feedback member 414, which may also be onboard the proximity sensor or separate from but in communication with the proximity sensor (e.g., sensory-feedback member 250, 254).

The foregoing description of use of the article(s) can be applied to the various example implementations described herein through minor modifications, which can be apparent to the person of skill in the art in light of the further disclosure provided herein. The above description of use, however, is not intended to limit the use of the article but is provided to comply with all necessary requirements of disclosure of the present disclosure. Any of the elements shown in the article(s) illustrated in FIGS. 1-4 or as otherwise described above may be included in an aerosol delivery device according to the present disclosure.

Many modifications and other implementations of the disclosure set forth herein will come to mind to one skilled in the art to which this disclosure pertains having the benefit of the teachings presented in the foregoing descriptions and the associated drawings. Therefore, it is to be understood that the disclosure is not to be limited to the specific implementations disclosed, and that modifications and other implementations are intended to be included within the scope of the appended claims. Moreover, although the foregoing descriptions and the associated drawings describe example implementations in the context of certain example combinations of elements and/or functions, it should be appreciated that different combinations of elements and/or functions may be provided by alternative implementations without departing from the scope of the appended claims. In this regard, for example, different combinations of elements and/or functions than those explicitly described above are also contemplated as may be set forth in some of the appended claims. Although specific terms are employed herein, they are used in a generic and descriptive sense only and not for purposes of limitation.

What is claimed is:

1. A control body coupled or coupleable with a cartridge that is equipped with a heating element and contains an aerosol precursor composition, the control body being coupled or coupleable with the cartridge to form an aerosol delivery device in which the heating element is configured to activate and vaporize components of the aerosol precursor composition, the control body comprising:

a housing; and within the housing, a flow sensor configured to detect a flow of air through at least a portion of the housing, the flow of air indicative of a puff of a user, and output an airflow-detected signal in response to the flow of air so detected;

a microprocessor configured to operate in an active mode in which the control body is coupled with the cartridge, the microprocessor in the active mode being configured to control the heating element to activate and vaporize components of the aerosol precursor composition; and a proximity sensor configured to detect a presence of the user nearby the control body without requiring any physical contact with the user, the proximity sensor comprising:

a source of excitation configured to drive a capacitive proximity sensor configured to measure a change in capacitance in the presence of the user; and a capacitance-to-digital converter (CPC) configured to convert the measured capacitance to a corresponding digital signal, the proximity sensor configured to output the corresponding digital signal as a proximity-detected signal in response to the presence of the user so detected, wherein the proximity sensor or microprocessor is further configured to control operation of at least one functional element of the aerosol delivery device in response to the presence of the user so detected, including the microprocessor configured to initiate operation in the active mode in response to both the proximity-detected signal and airflow-detected signal, and therein control the heating element to activate and vaporize components of the aerosol precursor composition.

2. The control body of claim 1, wherein the proximity sensor is configured to detect the presence of the user within a range that is user-programmable.

3. The control body of claim 1, wherein the proximity sensor being configured to detect the presence of the user includes being configured to obtain a measurement and detect the presence of the user in an instance in which the measurement satisfies a threshold, and wherein the threshold is user-programmable to depend on a specific user such that the proximity sensor is configured to detect the presence of the specific user.

4. The control body of claim 1, wherein the operation of the at least one functional element is user-programmable.

5. The control body of claim 1, wherein the proximity sensor or microprocessor being configured to control the at least one functional element includes being configured to control a sensory-feedback member to provide a user-perceptible feedback.

6. The control body of claim 1, wherein the proximity sensor or microprocessor being configured to control the at least one functional element includes being configured to alter a power state of the at least one functional element.

7. The control body of claim 6, wherein the proximity sensor or microprocessor being configured to alter the power state includes being configured to alter the power state of a communication interface that is coupled to the microprocessor and configured to enable wireless communication.

8. The control body of claim 1, wherein the proximity sensor or microprocessor being configured to control the at least one functional element includes being configured to control the at least one functional element to alter a locked state of the aerosol delivery device.

9. The control body of claim 1, wherein the proximity sensor includes first and second capacitive proximity sensors configured to measure respectively first and second capacitances that indicate respectively the presence of the user and a reference,
wherein the proximity sensor is further configured to calculate a level of perspiration of the user from the first and second capacitances, or output or output signals corresponding to the first and second capacitances for the microprocessor to calculate the level of perspiration of the user from the first and second capacitances, and
wherein the proximity sensor or microprocessor being further configured to control operation of the at least one functional element includes being further configured to control operation of the at least one functional element in response to the presence and level of perspiration of the user.

10. The control body of claim 1, wherein the proximity sensor or microprocessor being configured to control the at least one functional element includes being configured to upload to a service platform, data associated with the presence of the user detected by the proximity sensor.

11. A control body coupled or coupleable with a cartridge that is equipped with an atomizer and contains an aerosol precursor composition, the control body being coupled or coupleable with the cartridge to form an aerosol delivery device in which the atomizer is configured to activate and to produce an aerosol from the aerosol precursor composition, the control body comprising:
a housing; and within the housing,
a flow sensor configured to detect a flow of air through at least a portion of the housing, the flow of air indicative of a puff of a user, and output an airflow-detected signal in response to the flow of air so detected;
a microprocessor configured to operate in an active mode in which the control body is coupled with the cartridge, the microprocessor in the active mode being configured to control the atomizer to activate and to produce an aerosol from the aerosol precursor composition; and
a proximity sensor configured to detect a presence of the user nearby the control body without requiring any physical contact with the user, the proximity sensor comprising:
a source of excitation configured to drive a capacitive proximity sensor configured to measure a change in capacitance in the presence of the user; and
a capacitance-to-digital converter (CPC) configured to convert a measured capacitance to a corresponding digital signal, the proximity sensor configured to output the corresponding digital signal as a proximity-detected signal in response to the presence of the user so detected,
wherein the proximity sensor or microprocessor is further configured to control operation of at least one functional element of the aerosol delivery device in response to the presence of the user so detected,
including the microprocessor configured to initiate operation in the active mode in response to both the proximity-detected signal and airflow-detected signal, and therein control the atomizer to activate and to produce an aerosol from the aerosol precursor composition.

12. The control body of claim 11, wherein the proximity sensor being configured to detect the presence of the user includes being configured to obtain a measurement and detect the presence of the user in an instance in which the measurement satisfies a threshold, and
wherein the threshold is user-programmable to depend on a specific user such that the proximity sensor is configured to detect the presence of the specific user.

13. The control body of claim 11, wherein the proximity sensor or microprocessor being configured to control the at least one functional element includes being configured to alter a power state of a communication interface that is coupled to the microprocessor and configured to enable wireless communication.

14. The control body of claim 11, wherein the proximity sensor includes first and second capacitive proximity sensors configured to measure respectively first and second capacitances that indicate respectively the presence of the user and a reference,
wherein the proximity sensor is further configured to calculate a level of perspiration of the user from the first and second capacitances, or output or output signals corresponding to the first and second capacitances for the microprocessor to calculate the level of perspiration of the user from the first and second capacitances, and
wherein the proximity sensor or microprocessor being further configured to control operation of the at least one functional element includes being further configured to control operation of the at least one functional element in response to the presence and level of perspiration of the user.

* * * * *

UNITED STATES PATENT AND TRADEMARK OFFICE
CERTIFICATE OF CORRECTION

PATENT NO. : 11,291,252 B2
APPLICATION NO. : 14/975121
DATED : April 5, 2022
INVENTOR(S) : Rajesh Sur et al.

Page 1 of 1

It is certified that error appears in the above-identified patent and that said Letters Patent is hereby corrected as shown below:

In the Claims

In Column 16, Claim 1, Line 30, "capacitance-to-digital converter (CPC) configured" should read
-- capacitance-to-digital converter (CDC) configured --

In Column 18, Claim 11, Line 4, "capacitance-to-digital converter (CPC) configured" should read
-- capacitance-to-digital converter (CDC) configured --

Signed and Sealed this
Seventeenth Day of May, 2022

Katherine Kelly Vidal
*Director of the United States Patent and Trademark Office*